United States Patent
Jeong et al.

(10) Patent No.: US 11,925,721 B2
(45) Date of Patent: Mar. 12, 2024

(54) WATER STERILIZATION MODULE AND AIR COOLER INCLUDING THE SAME

(71) Applicant: SEOUL VIOSYS CO., LTD., Gyeonggi-do (KR)

(72) Inventors: Jae Hak Jeong, Gyeonggi-do (KR);
Woong Ki Jung, Gyeonggi-do (KR);
Hee Ho Bae, Gyeonggi-do (KR);
Byeong Cheol Ju, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 785 days.

(21) Appl. No.: 17/030,946

(22) Filed: Sep. 24, 2020

(65) Prior Publication Data
US 2021/0008241 A1    Jan. 14, 2021

Related U.S. Application Data

(63) Continuation of application No. PCT/KR2019/003479, filed on Mar. 26, 2019.

(30) Foreign Application Priority Data

Mar. 26, 2018    (KR) .................. 10-2018-0034272

(51) Int. Cl.
*A61L 2/26* (2006.01)
*A61L 2/10* (2006.01)
(Continued)

(52) U.S. Cl.
CPC .............. *A61L 2/26* (2013.01); *A61L 2/10* (2013.01); *C02F 1/325* (2013.01); *F24F 6/04* (2013.01);
(Continued)

(58) Field of Classification Search
CPC .......... A61L 2/26; A61L 2/10; A61L 2202/11; A61L 2202/121; A61L 2202/122;
(Continued)

(56) References Cited

U.S. PATENT DOCUMENTS 5,393,419 A   † 2/1995 Tiede
6,403,030 B1 * 6/2002 Horton, III ............. C02F 1/325
                                                       210/748.11
(Continued)

FOREIGN PATENT DOCUMENTS

CN       1450325 A      10/2003
CN     201309850 Y       9/2009
(Continued)

OTHER PUBLICATIONS

English Translation of Office Action from corresponding Korean Patent Application No. 10-2018-0034272, dated Jan. 12, 2023 (11 pages).

(Continued)

*Primary Examiner* — Justin M Jonaitis
(74) *Attorney, Agent, or Firm* — Perkins Coie LLP

(57) ABSTRACT

A water sterilization module includes a container including a water inlet and a water outlet and containing water therein, and a light source part mounted on a part of the container and irradiating sterilizing light into the container. The water inlet has a diameter larger than a diameter of the water outlet.

19 Claims, 7 Drawing Sheets

(51) Int. Cl.
*C02F 1/32* (2023.01)
*C02F 103/02* (2006.01)
*F24F 6/00* (2006.01)
*F24F 6/04* (2006.01)

(52) U.S. Cl.
CPC ...... *A61L 2202/11* (2013.01); *A61L 2202/121* (2013.01); *A61L 2202/122* (2013.01); *A61L 2202/123* (2013.01); *C02F 2103/023* (2013.01); *C02F 2303/04* (2013.01); *F24F 2006/006* (2013.01); *F24F 2006/008* (2013.01); *F24F 2006/046* (2013.01)

(58) Field of Classification Search
CPC ............... A61L 2202/123; C02F 1/325; C02F 2103/023; C02F 2303/04; F24F 6/04; F24F 2006/006; F24F 2006/008; F24F 2006/046
USPC .......................................................... 62/264
See application file for complete search history.

(56) References Cited

U.S. PATENT DOCUMENTS

| | | | | |
|---|---|---|---|---|
| 9,316,405 | B2* | 4/2016 | Moon | F24F 8/142 |
| 9,410,711 | B2* | 8/2016 | Wilson | C02F 1/325 |
| 2012/0234166 | A1* | 9/2012 | Markham | F24F 6/18 |
| | | | | 95/149 |
| 2012/0319311 | A1* | 12/2012 | Nutter | A61L 9/20 |
| | | | | 250/437 |
| 2015/0330643 | A1* | 11/2015 | Lee | F24F 6/06 |
| | | | | 210/243 |
| 2016/0089460 | A1* | 3/2016 | Jeong | A61L 2/10 |
| | | | | 250/455.11 |
| 2016/0235219 | A1* | 8/2016 | Aamodt | A61L 9/14 |
| 2017/0010010 | A1* | 1/2017 | Duvall | C02F 1/325 |

FOREIGN PATENT DOCUMENTS

| | | | | |
|---|---|---|---|---|
| CN | 205892799 U | | 1/2017 | |
| JP | H1147738 A | | 2/1999 | |
| JP | 2004003806 A | | 1/2004 | |
| JP | 2016-152899 | | 8/2016 | |
| KR | 20-0324735 | | 8/2003 | |
| KR | 20040082201 A | | 9/2004 | |
| KR | 10-0961090 | | 6/2010 | |
| KR | 10-2013-0031635 | | 3/2013 | |
| KR | 20150002647 U | | 7/2015 | |
| KR | 10-2016-0035265 | | 3/2016 | |
| KR | 20170116506 A | | 10/2017 | |
| KR | 201700116506 A | * | 10/2017 | |
| WO | WO-2014084492 A1 | * | 6/2014 | ............. F24F 6/025 |

OTHER PUBLICATIONS

Office Action issued in corresponding CN Application No. 201980035489.7, dated Jun. 9, 2022, English translation, 7 pages.
English Translation of Office Action from corresponding Chinese Patent Application No. 201980035489.7, dated Jan. 19, 2023 (21 pages).
International Search Report for International Application PCT/KR2019/003479, dated Jul. 22, 2019.

\* cited by examiner
† cited by third party

WATER STERILIZATION MODULE AND AIR COOLER INCLUDING THE SAME

CROSS-REFERENCE TO RELATED APPLICATIONS AND PRIORITY

The present application is a continuation of PCT Application No. PCT/KR2019/003479, filed on Mar. 26, 2019, which claims priority to and the benefit of Korean Application No. 10-2018-0034272, filed on Mar. 26, 2018, the disclosures of which are incorporated herein in their entireties.

FIELD

Embodiment of the present disclosure relate to a water sterilization module and an air cooler including the same.

BACKGROUND

A conventional air cooler is operated by supplying air to a wet nonwoven fabric using a blower fan. However, while such a conventional air cooler is in use, water in the nonwoven fabric naturally evaporates over time and germs or fungi may develop. An environment where germs or fungi thrive may result in a bad odor as well as mass proliferation of germs, microorganisms, and bacteria, which are harmful to the human body.

SUMMARY

According to one or more embodiments of the present disclosure, a water sterilization module is provided which prevents proliferation of germs, microorganisms and bacteria, and generation of a bad odor, and an air cooler employing the same.

In accordance with one aspect of the present disclosure, a water sterilization module includes: a container including a water inlet and a water outlet and receiving water therein; and a light source part mounted at a portion of the container to illuminate an interior of the container with sterilizing light, wherein the water inlet has a larger diameter than the water outlet.

In one embodiment, the water inlet may have a diameter twice as large as that of the water outlet.

In one embodiment, the container may include: a lower receptacle having an open top; and a cover covering the lower receptacle, and the light source part may be mounted on the cover.

In one embodiment, the water sterilization module may further include a first waterproof member disposed between a window of the light source part and a main body of the light source part to be closely coupled to the window and the main body.

In one embodiment, the cover may have an opening in which the light source part is mounted and the light source part may be mounted in the opening with a second waterproof member placed therebetween.

In one embodiment, the lower receptacle may include a bottom facing the cover and a sidewall extending upwards from the bottom, and the water outlet may be disposed on the bottom.

In one embodiment, the bottom may be inclined downwards from the sidewall towards the water outlet.

In one embodiment, the water outlet may be disposed at a center of the bottom.

In one embodiment, the water inlet may be separated from the water outlet in plan view.

In one embodiment, the water inlet may be disposed on the sidewall.

In one embodiment, the water inlet may be disposed on the cover.

In one embodiment, the water inlet may have an extension extending downwardly of the cover.

In one embodiment, a lower end of the extension may be placed outside an illumination angle of light emitted from the light source part.

In one embodiment, the lower end of the extension may have an inclined shape corresponding to the illumination angle of light emitted from the light source part.

In one embodiment, the light source part may include: a main body having a light outlet; a light source unit mounted on the main body and emitting the sterilizing light towards the light outlet; and a window mounted on the main body and disposed between the light source unit and an interior of the container.

In one embodiment, the main body may include: a head disposed inside the container; and a threaded portion passing through the container.

In one embodiment, the light source part may further include a holder coupled to the threaded portion outside the container.

In accordance with another aspect of the present disclosure, there is provided an air cooler employing the water sterilization module set forth above. The air cooler includes: a housing having an air inlet and an air outlet; a blower fan disposed in the housing to be adjacent to the air inlet; a moisture absorption member disposed between the blower fan and the air outlet; a water tank disposed in the housing to receive water therein; a pump supplying the water from the water tank to the moisture absorption member; and the water sterilization module disposed between the water tank and the moisture absorption member to sterilize the water.

In one embodiment, the air cooler may further include pipes disposed between the water tank and the water sterilization module and between the water sterilization module and the moisture absorption member, respectively. The pipe between the water tank and the water sterilization module may be connected to the water inlet of the water sterilization module and the pipe between the water sterilization module and the moisture absorption member may be connected to the water outlet.

DESCRIPTION OF DRAWINGS

FIG. 2A is a partial perspective view of the light source part of the water sterilization module according to one or more embodiments of the present disclosure; and FIG. 2B is an exploded perspective view of the light source part of the water sterilization module according to one or more embodiments of the present disclosure;

DETAILED DESCRIPTION

The present disclosure may be realized by various embodiments, and some exemplary embodiments of the present disclosure will be described in detail with reference to the accompanying drawings. However, it should be understood that the present disclosure is not limited to the following embodiments, and that various modifications, substitutions, and equivalent embodiments can be made by those skilled in the art without departing from the spirit and scope of the present disclosure.

Hereinafter, exemplary embodiments of the present disclosure will be described in detail with reference to the accompanying drawings.

One aspect of the present disclosure relates to a water sterilization module employed in various types of devices requiring sterilization of water and, more particularly, to a module for sterilizing water used in air coolers, humidifiers, water purifiers, dishwashers, and the like. Here, sterilization of water includes not only treatment to remove germs, microorganisms, bacteria, and the like from water, but also treatment to purify water and treatment to deodorize water.

The water sterilization module according to embodiments of the present disclosure may prevent proliferation of germs, microorganisms and bacteria, and generation of a bad odor. In addition, embodiments of the present disclosure provide a device including the water sterilization module set forth below.

Figure 1A:
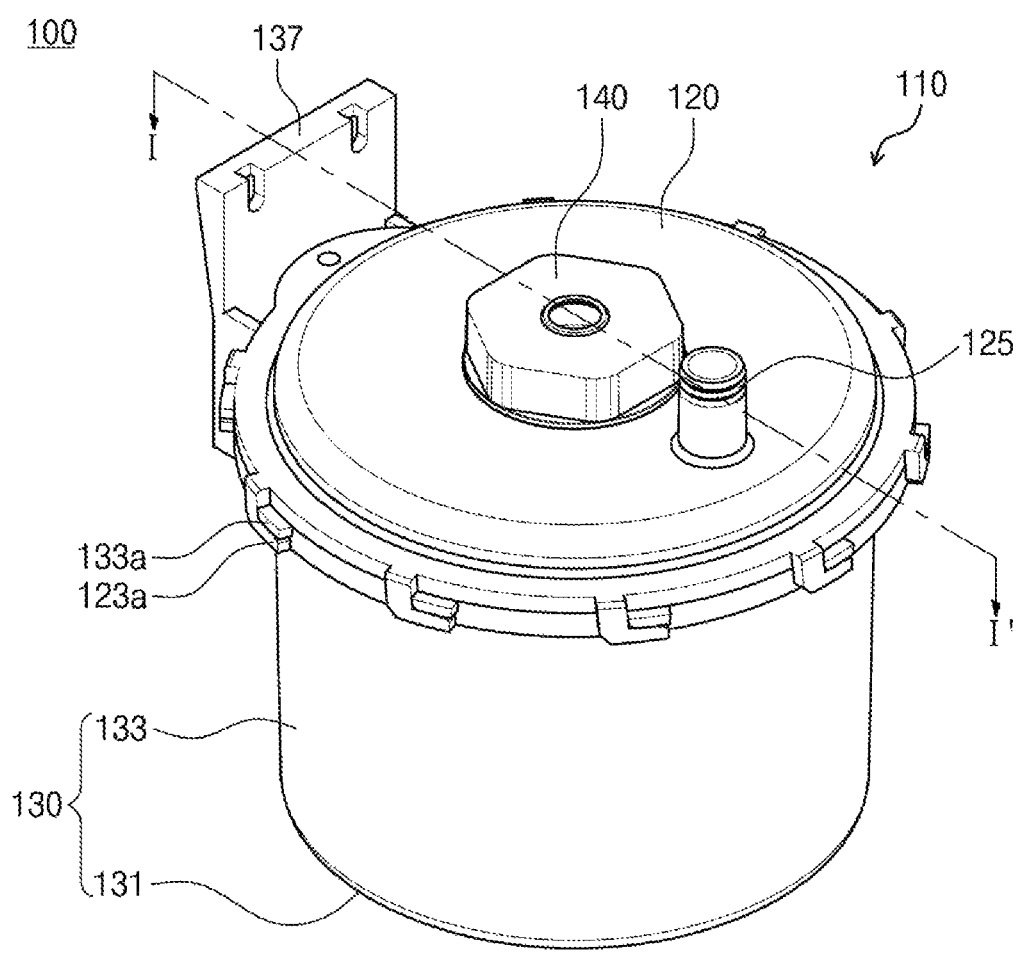
FIG. 1A is a perspective view of a water sterilization module according to one or more embodiments of the present disclosure.
Figure 1B:
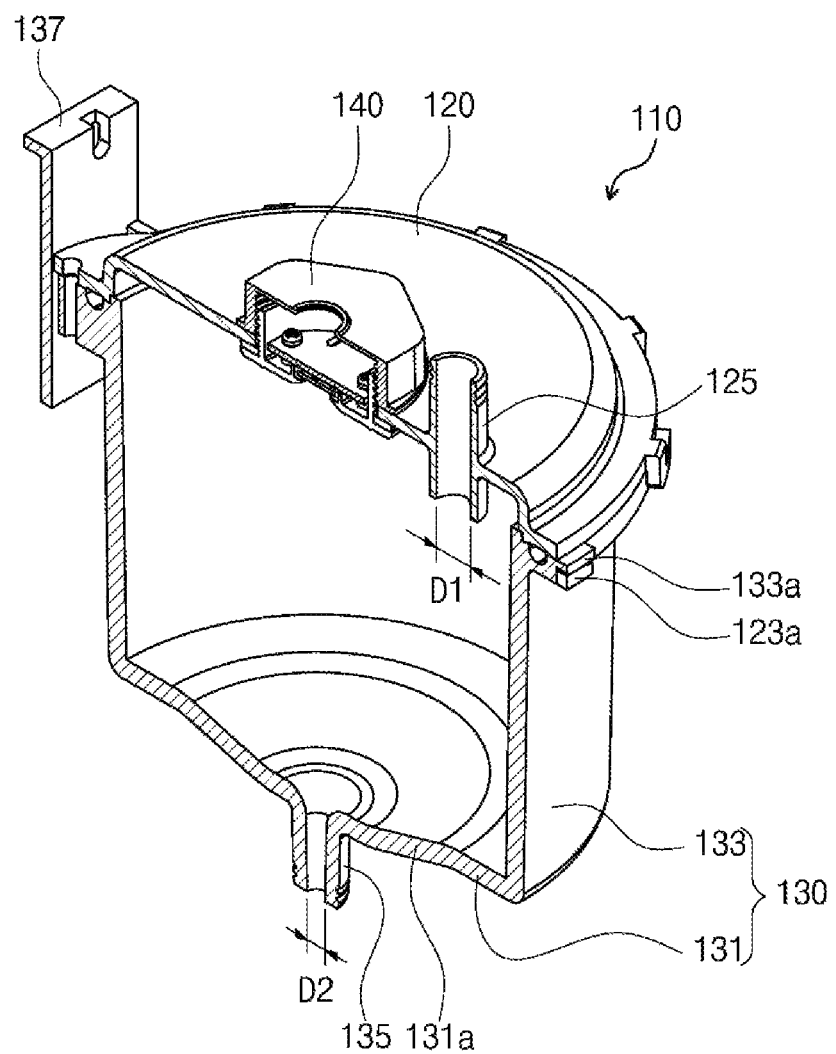
FIG. 1B is a partial perspective sectional view taken along I-I' of FIG. 1A.

FIG. 1A is a perspective view of a water sterilization module according to one or more embodiments of the present disclosure of the present disclosure and FIG. 1B is a partial perspective sectional view taken along line I-I' of FIG. 1.

Referring to FIG. 1A and FIG. 1B, the water sterilization module 100 includes a container 110 receiving water therein and a light source part 140 sterilizing water in the container 110.

The container 110 has an inner space to receive water therein and constitutes an external appearance of the water sterilization module 100. In one embodiment, an additional case or component may be further disposed outside the water sterilization module 100, although the container 110 is described as constituting the external appearance of the water sterilization module 100. In addition, when used in or with other devices, the water sterilization module 100 may further include additional components mounted thereon.

The container 110 may have a generally cylindrical shape, as shown in FIG. 1A and FIG. 1B. That is, the container 110 may have a circular shape in plan view and may have a generally rectangular shape in sectional view. In one embodiment, the overall shape of the container 110 in plan view may vary depending on in what device the water sterilization module 100 is used. The container 110 is not limited to a particular shape and the container 110 may have various overall shapes, so long as a sterilization target can be sufficiently sterilized therein.

The container 110 may be formed of various materials. In some embodiments, the container 110 may be formed of a metal, such as aluminum or stainless steel, without being limited thereto. In other embodiments, the container 110 may be formed of a polymer resin, particularly, a polymer resin that resistant to UV-induced deformation, cracking, and the like. The container 110 may be formed of one material, for example, a metal. Alternatively, the container 110 may be formed of two or more materials. For example, some portion of the container 110 may be formed of a metal, such as aluminum, and the other portion of the container 110 may be formed of a polymer resin.

The container 110 includes a water inlet 125 through which water is supplied to the inner space thereof and a water outlet 135 (shown in FIG. 1B) through which water is discharged therefrom.

In one embodiment, each of the water inlet 125 and the water outlet 135 may have a circular or elliptical cross-sectional shape. However, it will be understood that the present disclosure is not limited thereto and each of the water inlet 125 and the water outlet 135 may have various cross-sectional shapes, for example, a polygonal shape. Here, the cross-section of each of the water inlet 125 and the water outlet 135 may be obtained by a plane cutting through each of the water inlet 125 and the water outlet 135 at a right angle with respect to a direction in which the water inlet 125 extends or a direction in which a flow path is formed.

Although not shown in the drawings, a separate pipe may be further provided to the water inlet 125 and/or the water outlet 135. Here, the separate pipe may be connected to the water inlet 125 and the water outlet 135 via a nozzle. Here, the nozzle may be coupled to the water inlet 125 and/or the water outlet 135 by any suitable coupling method, for example, a screw engagement.

In some embodiments, the container 110 includes a lower receptacle 130 having an open top, and a cover 120 covering the lower receptacle 130.

The lower receptacle 130 is provided in the form of a bowl with an open top to receive water therein. The lower receptacle 130 includes a bottom 131 facing the cover 120 and a sidewall 133 extending upwards from the bottom 131.

As shown in FIG. 1B, the bottom 131 may be provided in the form of a generally flat disk and the sidewall 133 may be provided in the form of a pipe extending upwards along the outer periphery of the disk. The sidewall 133 may have a stepped portion at an upper end thereof to be easily coupled to the cover 120. In addition, the sidewall 133 may be provided at an upper side thereof with an additional mount to couple another device or an additional component thereto.

The cover 120 is mounted on the upper end of the lower receptacle 130. The cover 120 is not limited to a particular shape and may have various shapes depending upon the shape of the lower receptacle 130. The cover 120 may be detachably mounted on the upper end of the lower receptacle 130.

The cover 120 completely covers the upper end of the lower receptacle 130. The cover 120 may be provided in the form of a generally flat plate and may have a stepped portion formed at an edge thereof and partially bent downwards, as shown in FIG. 1B.

The cover 120 and the lower receptacle 130 may be provided with fastening members by which the cover 120 is coupled to or separated from the lower receptacle 130. The fastening member may include, for example, hooks, screws, insertion grooves, and protrusions, whereby the cover 120 can be coupled to the lower receptacle 130 in various ways. In one embodiment, when fastening members provided to the cover 120 and the lower receptacle 130 are referred to as first and second fastening members 123a, 133a, respectively, the first and second fastening members 123a, 133a may protrude from the cover 120 and the lower receptacle 130, respectively, to be engaged with each other. The first fastening member 123a may protrude from the surface of the cover 120 to be bent in one direction, whereby the first fastening member 123a can be caught by the second fastening member 133a protruding from the sidewall 133 of the lower receptacle 130 to allow the cover 120 to be coupled to the lower receptacle 130, upon rotation of the cover 120 in one direction while pressing the cover 120 downwards.

The cover 120 has an opening in which the light source part 140 is mounted. The light source part 140 may be mounted at a location corresponding to the opening. Although the location of the opening in the cover 120 is not particularly limited, the opening may be formed at the center of the cover 120 such that the interior of the lower receptacle 130 can be illuminated with as much light as possible. That is, when the cover 120 has a circular cross-sectional shape, the light source part 140 may be disposed at or near the center of the circle. The light source part 140 will be described in detail further below.

Although the water inlet 125 and the water outlet 135 are not particularly limited to particular locations, the water inlet 125 may be formed on the cover 120 and the water outlet 135 may be formed on the bottom 131 of the lower receptacle 130 in the water sterilization module 100 according to the embodiment.

The water inlet 125 may be coupled to the cover 120 to be connected to the inner space of the container 110. The water inlet 125 vertically passes through the cover 120. Here, the water inlet 125 has an extension extending downwardly of the cover 120. Accordingly, a lower end of the water inlet 125, that is, an end of the extension, may be placed below a lower surface of the cover 120, particularly, below a lower surface of the light source part 140 mounted on the cover 120. With the structure where the end of the water inlet 125 is placed below the light source part 140 mounted on the cover 120, water can be prevented from splashing onto the light source part 140 and adversely affecting the light source part 140, when water is introduced into the lower receptacle 130 from the end of the water inlet 125.

The water outlet 135 is formed on the bottom 131. Although the water outlet 135 is not limited to a particular location on the bottom 131, the water outlet 135 may be formed at the center of the bottom 131. That is, when the bottom 131 has a circular cross-sectional shape, the water outlet 135 may be formed at or near the center of the circle.

In some embodiments, the bottom 131 around the water outlet 135 may have an inclined portion 131a to facilitate discharge of water through the water outlet 135. That is, the bottom 131 may be inclined downwards from the sidewall 133 towards the water outlet 135.

In some embodiments, the water inlet 125 and the water outlet 135 have a structure that allows water introduced into the container 110 to stay in the container 110 for a predetermined period of time. If water introduced into the container 110 through the water inlet 125 is immediately discharged through the water outlet 135, the water cannot be sufficiently sterilized by the light source part 140. Accordingly, the water inlet 125 or the water outlet 135 may be placed or shaped to allow water to stay in the container 110 for a sufficient period of time in consideration of the irradiance or intensity of sterilizing light emitted from the light source part 140.

In some embodiments, the water inlet 125 may be separated from the water outlet 135 in plan view such that water can stay in the container 110 for a sufficient period of time. If the water inlet 125 and the water outlet 135 are disposed at the same location in plan view, water introduced through the water inlet 125 is more likely to be immediately discharged through the water outlet.

In some embodiments, the water inlet 125 and the water outlet 135 may have different sizes to control the moving speed and residence time of water introduced into the container 110. In other embodiments, the water inlet 125 may have a larger diameter than the water outlet 135. When the water inlet 125 has a relatively large diameter as compared with the water outlet 135, introduction of water into the container 110 is relatively easy, as compared with discharge of water from the container 110. Accordingly, the residence time of water in the container 110 can be increased.

More specifically, an inner diameter D1 of the water inlet 125 may be larger than an inner diameter D2 of the water outlet 135. When the inner diameter D1 of the water inlet 125 is larger than the inner diameter D2 of the water outlet (135), resistance is applied to water to be discharged from the container 110 due to a smaller diameter of the water outlet 135. As a result, a flow rate of water at the water outlet 135 is smaller than the flow rate of water at the water inlet 125. When the flow rate of water at the water inlet 125 is referred to as a first flow rate and the flow rate of water at the water outlet 135 is referred to as a second flow rate, the second flow rate is smaller than the first flow rate. Accordingly, discharge of water through the water outlet 135 is delayed due to resistance at the water outlet 135, thereby causing water to stay longer in the container 110. The longer water stays in the container 110, the longer exposure time of water to light emitted from the light source part 140 is as described below. As the exposure time of water to light emitted from the light source part 140 increases, the cumulative amount of light radiated to a given amount of water increases, thereby improving efficiency in sterilization of water. Although not shown in the drawings, the internal shape of the container 110 may vary to increase the time that water stays in the container 110 while allowing the water inlet 125 and the water outlet 135 to have different sizes.

In some embodiments, a ratio of the diameter D1 of the water inlet 125 to the diameter D2 of the water outlet 135 may be about 2:1.

The light source part 140 is mounted on the container 110 and sterilizes water in the container 110 by illuminating the water with a sterilizing light. The light source part 140 may be disposed at any suitable location that allows the water in the container 110 to be evenly illuminated with the sterilizing light. In one embodiment, the light source part 140 may be mounted on the cover 120.

Figure 2A:
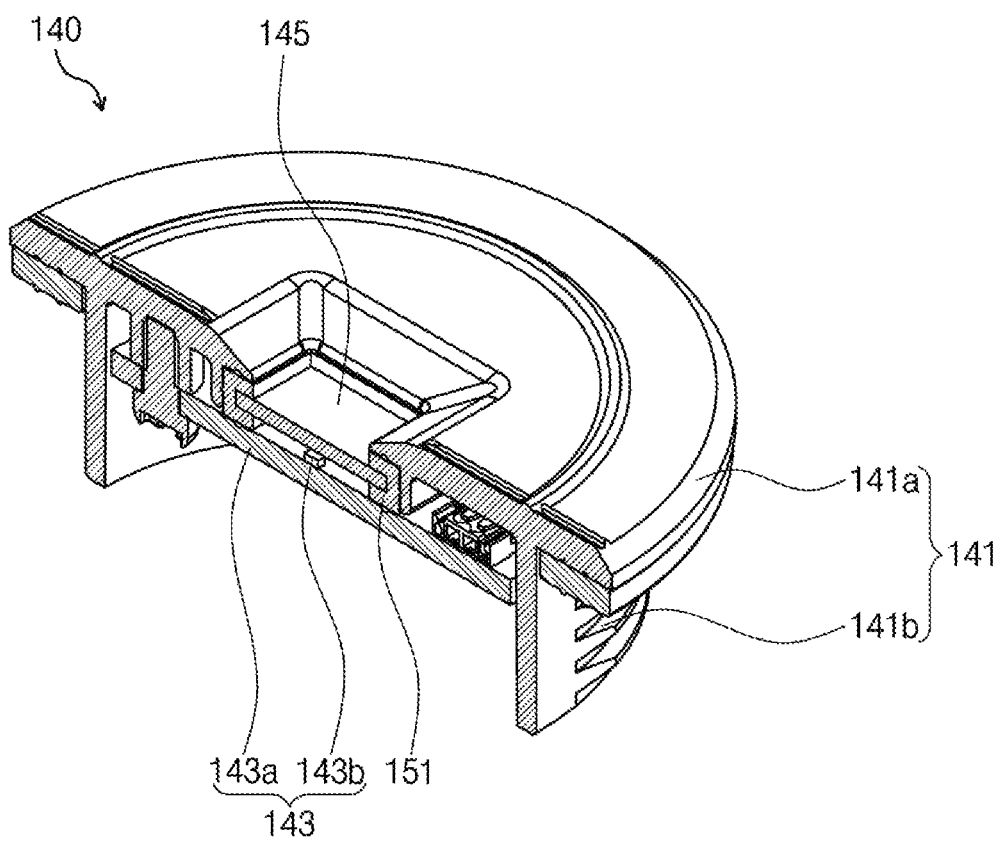
FIG. 2A and FIG. 2B show a light source part according to one or more embodiments of the present disclosure.
Figure 2B:
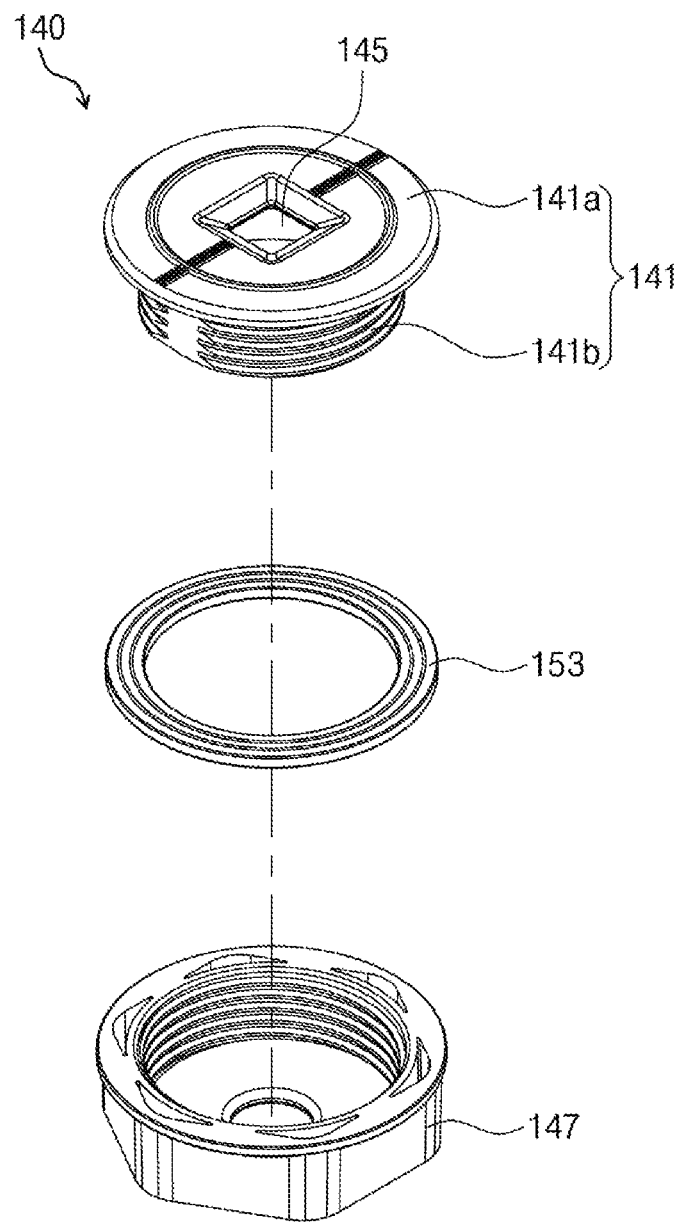

FIG. 2A and FIG. 2B illustrate a light source part according to one embodiment of the present disclosure. Specifically, FIG. 2A is a partial perspective view of the light source part of the water sterilization module according to the embodiment and FIG. 2B is an exploded perspective view of the light source part of the water sterilization module according to the embodiment. In FIG. 2A and FIG. 2B, unlike in FIG. 1A and FIG. 1B, the light source part 140 is turned upside down for convenience of explanation.

Referring to FIG. 1A, FIG. 1B, FIG. 2A, and FIG. 2B, the light source part 140 includes a main body 141 having a light outlet, a light source unit 143 mounted on the main body 141 and emitting the sterilizing light towards the light outlet, and a window 145 mounted on the main body 141 to be disposed between the light source unit 143 and the interior of the container 110.

The main body 141 may include a head 141a facing the interior of the container 110 and a threaded portion 141b extending from the head 141a.

In plan view, the head 141a has an opening, which corresponds to a passage along which the sterilizing light from the light source unit 143 passes through the head 141a. The opening may have a sidewall having a predetermined slope in order to minimize loss of light emitted from the light source unit 143.

The threaded portion 141b vertically protrudes from the head 141a and may have a thread formed on an outer surface thereof. The thread is screwed onto a holder 147 described below.

The head 141a may have a plurality of protrusions, depressions, and/or stepped portions at which the light source unit 143 is seated. A separate fastening member may be further provided to secure the light source unit 143 to the head 141a. In some embodiments, the light source part 140, particularly, a substrate 143a described below, is placed on the stepped portions of the main body 141 and is coupled to the main body 141 by any suitable fastening member, for example, a hook, a screw, an insertion groove and protrusion, or the like. For example, the light source unit may be coupled to the head 141a via one or more screws.

The light source unit 143 includes a substrate 143a and at least one light source 143b mounted on the substrate 143a.

The light source 143b emits sterilizing light and may be implemented by a light emitting diode.

The substrate 143a may be provided in the form of a plate. The substrate 143a may have a circular, elliptical, or rectangular shape, without being limited thereto. The substrate 143a may have, for example, a rectangular shape elongated in a predetermined direction.

The substrate 143a is electrically connected to the light source 143b and provides electric power supplied from an external power source to the light source 143b. For example, the substrate 143a may be a circuit board, a printed circuit board (PCB), a metal substrate, or a ceramic substrate. However, these are given by way of example only and the kind and material of the substrate 143a are not particularly restricted so long as electrical connection between the substrate 143a and the light source 143b can be achieved.

At least one (for example, multiple) light source 143b may be disposed on one surface of the substrate 143a. When the light source part includes one light source 143b, the light source 143b may be disposed at any suitable location of the substrate 143a, for example, at the center of the substrate 143a. When the light source part includes multiple light sources 143b, the light sources 143b may be arranged in various manners, for example, in a random manner or in a specific pattern, such as a straight line and a zigzag pattern. Here, the light source 143b may be disposed such that as much light as possible is radiated downwards.

When the light source part includes multiple light sources 143b, the light sources 143b may emit light at the same or different wavelengths. For example, in one embodiment, some light sources 143b may emit light at a specific wavelength in the UV region and the other light sources 143b may emit light at another wavelength in the UV region.

When a light emitting diode is used as the light source 143b of the light source part 140, the light emitting diode may be mounted on the substrate 143a. Here, the light emitting diode may be disposed on the substrate 143a in the form of a surface-mountable injection-molded lead frame package, in a through-hole mounting manner, or in the form of a bare chip or a flip chip. Alternatively, the light emitting diode may be attached to an additional substrate 143a to improve heat dissipation properties and electrical properties of the light emitting diode.

The light source 143b may emit sterilizing light having a sterilization function to minimize proliferation of bacteria. For example, the light source 143b may emit light in the UV region. In one embodiment, the light source 143b may emit light at a wavelength of about 100 nm to about 405 nm, which is capable of destroying microorganisms and the like. In another embodiment, the light source 143b may emit light at a wavelength of about 100 nm to about 280 nm. In further another embodiment, the light source 143b may emit light at a wavelength of 180 nm to about 280 nm. In yet another embodiment, the light source 143b may emit light at a wavelength of about 250 nm to about 260 nm. UV light in these wavelength ranges has high sterilizing power and can destroy up to about 99% of bacteria, such as *Escherichia coli, Bacillus diphtherias,* and *Bacillus dysenteriae*, at an intensity of, for example, 100 µW per cm$^2$. In addition, UV light in these wavelength ranges can destroy bacteria that cause food poisoning, such as pathogenic *Escherichia coli, Staphylococcus aureus, Salmonella Weltevreden, S. Typhumurium, Enterococcus faecalis, Bacillus cereus, Pseudomonas aeruginosa, Vibrio parahaemolyticus, Listeria monocytogenes, Yersinia enterocolitica, Clostridium perfringens, Clostridium botulinum, Campylobacter jejuni,* or *Enterobacter sakazakii*.

The window 145 (shown in FIGS. 2A and 2B) may be transparent or at least translucent to transmit light from the light source 143b therethrough and to protect the light source 143b. In particular, the window 145 may be formed of quartz or an organic polymer material. Here, since the wavelength of light absorbed/transmitted by/through the organic polymer material depends on the type of monomers used, the method used to form the organic polymer material, and the condition in which the organic polymer material is formed, the organic polymer material may be selected in consideration of wavelengths of light emitted from the light sources 143b. For example, polymer resins such as poly (methyl methacrylate) (PMMA), polycarbonate (PC), polyvinyl alcohol (PVA), polypropylene (PP), and low-density polyethylene (PE) absorb little or no UV light, whereas polymer resins, such as polyester resins, can absorb UV light. In consideration of the absorption wavelength, the window 145 may be preferably formed of a material that absorbs UV lightless than polymer resins. In one embodiment, the window 145 may include one selected from the group of quartz, fused silica, poly(methyl methacrylate), and a fluorine-based polymer.

The light source part 140 may further include a first waterproof member 151 disposed between the opening of the main body 141 and the window 145. The first waterproof member 151 may be disposed along an edge of the window 145 and may be placed at a stepped portion or a depression formed on the sidewall of the opening of the main body 141. The first waterproof member 151 may have substantially the same size and shape as the window 145.

Here, the first waterproof member 151 may have a closed shape to separate a space facing the container 110 from a space facing away from the container 110 with respect to the window 145 when coupled to the substrate 143a and the main body 141 later. In some embodiments, the first waterproof member 151 may be provided in the form of an O-ring.

The first waterproof member 151 may be formed of a soft elastic material. When the first waterproof member 151 is formed of an elastic material, the first waterproof member 151 can be compressed by the main body 141 and the substrate 143a upon coupling the lower receptacle 130 to the substrate 143a by screw fastening or the like, thereby preventing intrusion of water or moisture into the light source unit 143.

The elastic material forming the first waterproof member 151 may include a silicone resin. However, it will be understood that the present disclosure is not limited thereto and the first waterproof member 151 may be formed of any other material that can stably seal the cover 120 and the lower receptacle 130. For example, natural or synthetic rubber or other elastic organic polymer materials may be used as the elastic material.

In the water sterilization module 100 according to one or more embodiments, the light source part 140 may be mounted on the cover 120 by screwing the threaded portion 141b onto a holder 147 outside the container 110.

The holder 147 has a thread formed on an inner surface thereof and corresponding to the thread of the threaded portion 141b of the main body 141 to be screwed onto the threaded portion 141b of the main body 141. In other words, the threaded portion 141b of the main body 141 passes through the opening of the cover 120 from the inside of the container 110 to the outside of the container 110 to be screwed onto the holder 147 outside the container 110. Although the main body 141 is shown as coupled to the holder 147 by the screw engagement in this embodiment, it will be understood that the present disclosure is not limited thereto and the main body 141 may be coupled to the holder 147 by any other suitable method.

A second waterproof member 153 may be disposed between the holder 147 and the main body 141 to prevent intrusion of water or moisture into the light source unit 143 from the container 110. The second waterproof member 153 is disposed along an edge of the threaded portion 141b of the main body 141. The second waterproof member 153 may be placed between the cover 120 and the head 141a of the main body 141 in sectional view. Here, the second waterproof member 153 may have a closed shape to separate and seal a space defined by the cover 120, the lower receptacle 130, and the light source part 140 from the exterior of the space. In some embodiments, the second waterproof member 153 may be provided in the form of an O-ring.

The second waterproof member 153 may also be formed of a soft elastic material. When the second waterproof member 153 is formed of an elastic material, the second waterproof member 153 can be compressed by the main body 141 and the substrate 143a upon coupling the threaded portion 141b of the main body 141 to the holder 147 by screw engagement or the like, thereby separating the space defined by the cover 120, the lower receptacle 130, and the substrate 143a from the exterior of the space. As a result, the second waterproof member 153 can prevent intrusion of water or moisture into the light source part 140, that is, into the light source unit 143.

The elastic material forming the second waterproofing member 153 may include a silicone resin. However, it will be understood that the present disclosure is not limited thereto and the second waterproofing member 151 may be formed of any other material that can stably seal the cover 120 and the lower receptacle 130. For example, natural or synthetic rubber and other elastic organic polymer materials may be used as the elastic material. In one embodiment, the first waterproofing member and the second waterproofing member 153 may be formed of the same or different materials. Specifically, each of the first and second waterproofing members may be formed of Viton, ethylene propylene rubber (E.P.R), Teflon, or Kalrez, without being limited thereto.

The water sterilization module having the structure set forth above can effectively sterilize water by easily removing bacteria and microorganisms from the water. According to one embodiment, since the water outlet 135 has a smaller diameter than the water inlet 125, the flow rate of water discharged from the container 110 through the water outlet 135 is smaller than the flow rate of water introduced into the container 110 through the water inlet 125, thereby allowing water to stay in the container 110 for a predetermined period of time or more. As a result, water in the container 110 can be exposed to light from the light source unit 143 for an increased period of time, thereby allowing increase in cumulative amount of light radiated to water and thus improvement in water treatment efficiency.

Figure 3A:
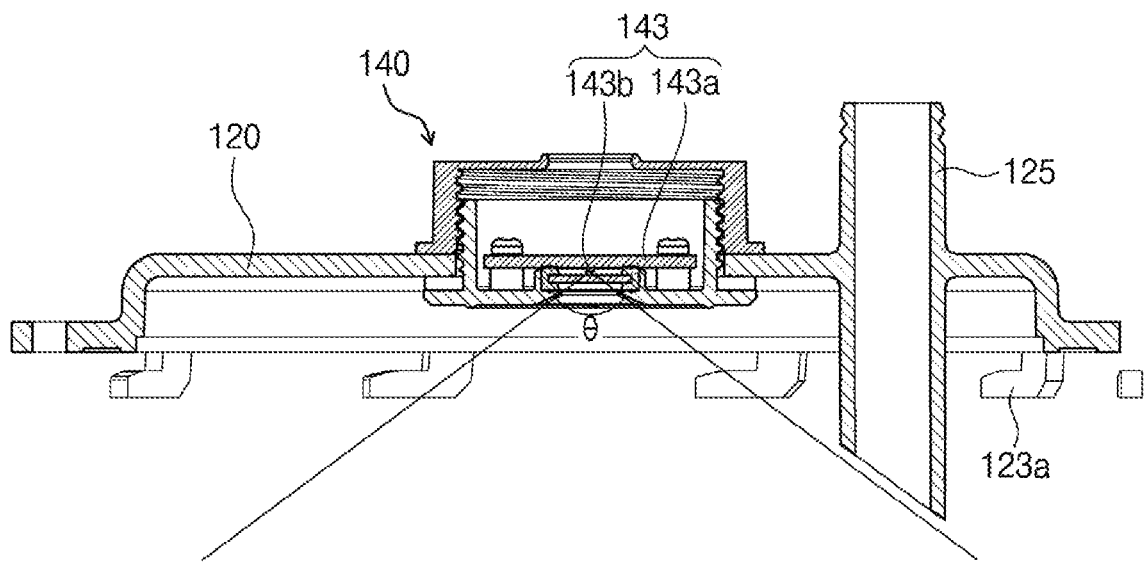
FIG. 3A is a sectional view of the water sterilization module according to one or more embodiments of the present disclosure, showing different shapes of a water inlet.
Figure 3B:
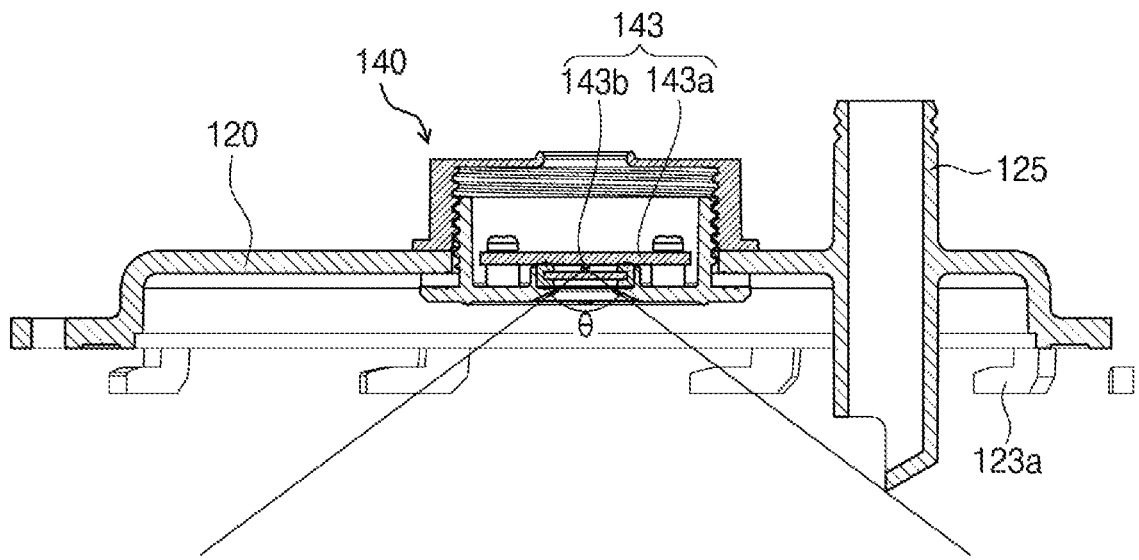
FIG. 3B is another sectional view of the water sterilization module according to one or more embodiments of the present disclosure, showing different shapes of a water inlet.

In one embodiment, the shape of the water inlet may vary, as needed. FIG. 3A and FIG. 3B are sectional views of the water sterilization module according to the embodiment of the present disclosure, showing different shapes of the water inlet.

Referring to FIG. 3A and FIG. 3B, the water inlet 125 may be disposed in a region that does not interfere with a route along which light from the light source part 140 travels into the container 110. In particular, a lower end of the water inlet 125 may be disposed outside an illumination area of the light source part.

In one embodiment, light is emitted downwards from the light source part 140 over a predetermined angle. For example, in one embodiment, the light source 143b may emit light at a predetermined illumination angle θ. In one embodiment, the illumination angle θ of each light source 143b may be 110 degrees or more. In another embodiment, the illumination angle θ of each light source 143b may range 110 degrees to 150 degrees. In further another embodiment, the illumination angle θ of each light source 143b may be 150 degrees or more, or may be close to 180 degrees. However, light emitted from the light source unit 143 can be partially blocked depending on the shape of the opening of the main body 141, thereby causing limitation in illumination angle. As a result, the actual illumination angle θ of each light source 143b can be less than 180 degrees, as shown in the drawings.

If the water inlet 125 has a downward extension which extends long enough to be placed within the illumination angle, light from the light source unit 143 can be partially blocked by the water inlet 125, causing reduction in area of water exposed to light and thus reduction in sterilization effect. In one embodiment, the water inlet 125 has an extension having a length that allows the water inlet 125 to be placed outside the illumination area of the light source part so as to prevent such a problem.

To this end, the lower end of the water inlet 125 may have an inclined shape corresponding to the illumination angle of light emitted from the light source part 140, as shown in FIG. 3A. Specifically, the lower end of the water inlet 125 may be inclined to be placed outside the illumination area of the light source part 140 and to be parallel to the illumination direction of light in consideration of the illumination angle of light. This structure is provided to avoid the water inlet 125 from concealing the illumination area as much as possible. That is, the lower end of the water inlet 125 may be inclined in a direction away from the light source 143b in sectional view.

In addition to the inclined structure, the lower end of the water inlet 125 may be bent to allow water from the water inlet 125 to proceed into the space within the illumination angle as much as possible, as shown in FIG. 3B. Specifically, the lower end of the water inlet 125 may be bent towards the center of the container 110 in sectional view. In this way, upon entering the container 110, water can be directed towards the center of the container 110 along the bent lower end of the water inlet 125 and thus can be exposed to light for an increased period of time. Accordingly, the water sterilization module can ensure further improved sterilization.

That is, according to the present disclosure, interference with the light path by the water inlet 125 can be minimized and exposure of water to light emitted from the light source 143b can be maximized, thereby improving photo-sterilization efficiency.

Although not shown in the drawings, in the water sterilization module 100 according to one embodiment, the water inlet 125 may be disposed at various locations without altering the concepts of the present disclosure. For example, the water inlet 125 may be disposed at the lower receptacle 130 rather than at the cover 120. In this case, the water inlet 125 may be disposed at an upper side of the sidewall 133.

Figure 4:
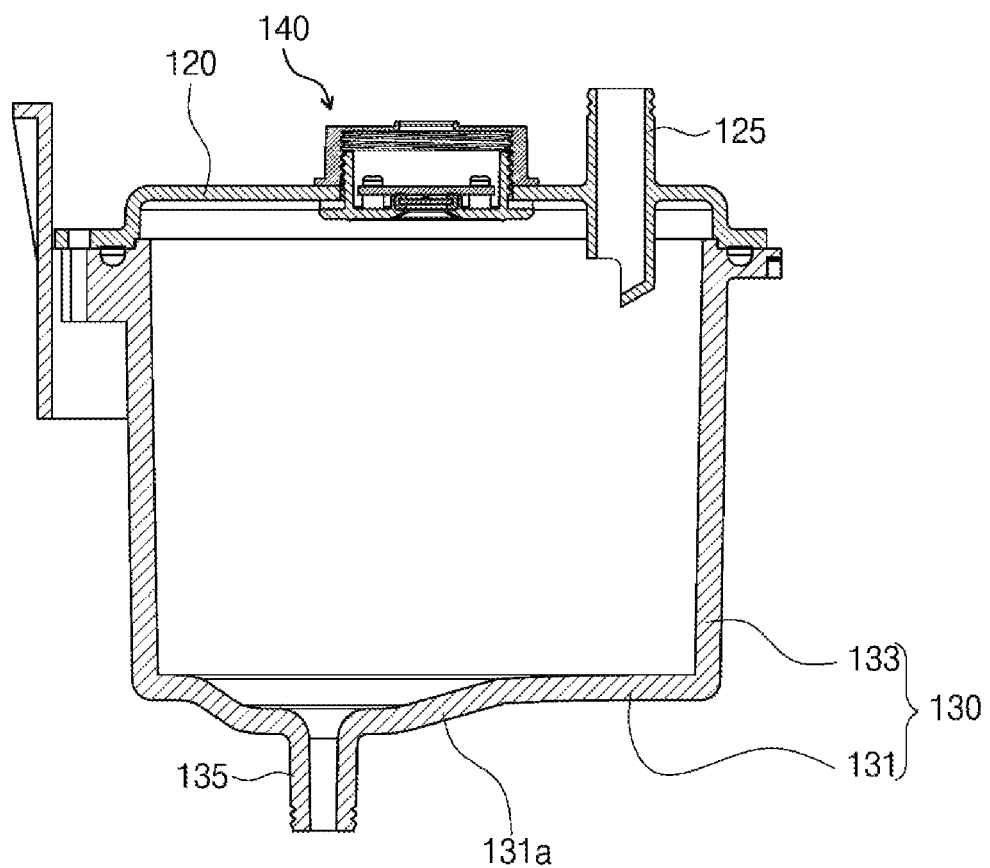
FIG. 4 is a sectional view of the water sterilization module according to one or more embodiments of the present disclosure, showing a different location of a water outlet.

In one embodiment, like the water inlet, the water outlet may be disposed at various locations. FIG. 4 is a sectional view of the water sterilization module according to the embodiment of the present disclosure, showing a different location of the water outlet.

Referring to FIG. 4, the water outlet 135 may be disposed at a side of the lower receptacle 130 rather than at the center of the lower receptacle 130. In this embodiment, the water outlet 135 may be disposed at a location separated as far as possible from the water inlet 125. With this arrangement in which the water outlet 135 is separated as far as possible from the water inlet 125, water introduced into the container 110 through the water inlet 125 can stay in the container 110 for an increased period of time before being discharged from the container 110 through the water outlet 135. Accordingly, water in the container 110 can be exposed to light for as long a period of time as possible, thereby allowing improvement in the sterilization effect.

Although not shown in the drawings, the water outlet 135 may be disposed on the sidewall of the lower receptacle rather than on the bottom 131. In this case, the water outlet 135 may be disposed at a lower end of the sidewall of the lower receptacle.

The water sterilization module having the structure set forth above may be employed in various types of devices requiring sterilization of water. For example, the water sterilization module may be employed in air coolers, humidifiers, water purifiers, dishwashers, and the like.

Now, the present disclosure will be described by way of an example in which the water sterilization module according to the embodiment of the present disclosure is employed in an air cooler. However, it will be understood that the present disclosure is not limited thereto.

Figure 5:
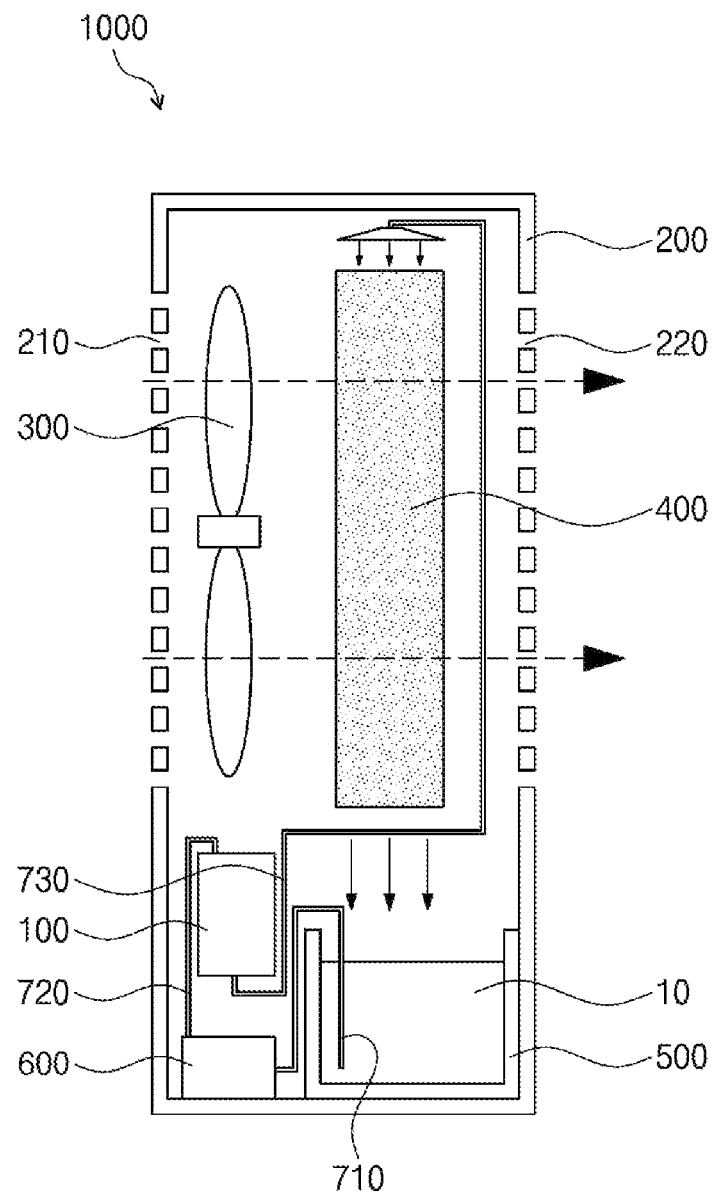
FIG. 5 is a conceptual diagram of an air cooler employing the water sterilization module according to one or more embodiments of the present disclosure.

FIG. 5 is a conceptual view of an air cooler employing the water sterilization module according to the embodiment of the present disclosure.

Referring to FIG. 5, an air cooler 1000 according to one or more embodiments of the present disclosure includes a housing 200, a blower fan 300 disposed inside the housing 200, a water/moisture absorption pad 400, a water tank 500, a pump 600, and the water sterilization module 100 set forth above.

The housing 200 constitutes an external appearance of the air cooler 1000 and has an inner space for cooling air. Although the housing 200 has been described as constituting the external appearance of the air cooler 1000, an additional case or component may be further disposed outside the air cooler 1000.

The housing 200 has an air inlet 210 formed at one side thereof to introduce air into the housing therethrough and an air outlet 220 formed at the other side thereof to discharge air from the housing therethrough. In the inner space of the housing 200, a flow path along which air introduced through the air inlet 210 is moved to the air outlet 220 is created. In FIG. 5, the flow path is indicated by a dotted arrow.

Although the housing 200 may have various shapes, the housing 200 is shown as having a rectangular shape in FIG. 5, for convenience of description.

In the description of the present disclosure, for convenience of description, the air inlet 210 is shown as being placed at a front side (left in the drawing) of the housing and the air outlet 220 is shown as being placed at a rear side (right in the drawing) of the housing when the air inlet 210, the inner space, and the air outlet 220 are arranged in a line. However, it will be understood that these expressions of spatial orientations are given for convenience of description and are to be construed as indicating relative orientations, which are defined by the actual mounting orientation of the housing.

Air moved through the air inlet 210 and the air outlet 220 is a cooling target. In one embodiment, the air cooler 1000 serves to provide cool air in summer when the atmospheric temperature is high.

In some embodiments, the air inlet 210 is provided in the form of an opening that allows air to be introduced into the housing 200 therethrough. The air cooler may further include a front net attached to the air inlet 210 to guide air flow, conceal the interior of the housing 200 from the outside, or protect the interior of the housing 200 from external influence. Here, the front net may be detachable from the air inlet 210 and may include at least one rib and a support securing the rib. The rib may be provided in the form of a plate extending in one direction or may be provided in the form of a radial frame, such as a fan net, or a concentric frame in front view.

Similarly, the air outlet 220 is provided in the form of an opening that allows air to be discharged from the housing 200 therethrough. The air cooler may further include a back net attached to the air outlet 220 to guide movement of air, conceal the interior of the housing 200 from the outside, or protect the interior of the housing 200 from external influence. The back net may be detachable from the air outlet 220 and may include at least one rib and a support securing the rib. The rib may be provided in the form of a plate extending in one direction or may be provided in the form of a radial frame, such as a fan net, or a concentric frame in front view.

The housing 200 contains components for cooling air introduced thereinto through the air inlet 210, for example, the blower fan 300, the water/moisture absorption pad 400, the water tank 500, and the water sterilization module 100 set forth above.

The blower fan 300 is disposed adjacent to the air inlet 210 and serves to blow external air into the housing 200.

The blower fan 300 includes a motor and multiple blades connected to the motor. Upon driving the fan using the motor, air is introduced into the housing 200 through the air inlet 210 and then moved towards the air outlet 220. However, it will be understood that the present disclosure is not limited thereto and the blower fan 300 may be any known blower fan that can force air to flow.

The moisture absorption member 400 is disposed at one side of the blower fan 300. Specifically, the moisture absorption pad 400 is disposed between the blower fan 300 and the air outlet 220.

The moisture absorption member 400 is formed of a material that can easily absorb moisture and has a large surface area. The moisture absorption member 400 may be formed of, for example, a nonwoven fabric or a sponge, or may have a plate shape bent multiple times to increase the surface area thereof. In particular, when the moisture absorption member 400 is provided in the form of a fine mesh, such as a nonwoven fabric or a sponge, water can be effectively held between strands of the mesh while a water film can be evenly formed on the surface of the mesh. Accordingly, a contact area between air and water occurs can be increased.

Here, the moisture absorption member 400 is adapted to allow air supplied by the blower fan 300 to pass therethrough. The air supplied by the blower fan 300 contacts water in the moisture absorption member 400 while passing through the moisture absorption member 400 having a large surface area, whereby the water evaporates by absorbing thermal energy from the air. As such, since the thermal energy of the air is transferred to the water, the air passing through the moisture absorption member 400 is cooled by heat of vaporization of the water.

In one embodiment, the moisture absorption member 400, which contacts moisture at all times, may be treated with an antibacterial or bactericidal coating to minimize proliferation of germs, microorganisms, and bacteria.

The water tank 500 adapted to receive water 10 therein is disposed under the moisture absorption member 400. The water tank 500 may be disposed below the moisture absorption member 400 to receive water falling from the moisture absorption member 400. Although the moisture absorption member 400 is shown as spaced apart from the water tank 500 in FIG. 5, it will be understood that the present disclosure is not limited thereto and the moisture absorption member 400 may be partially immersed in the water 10 in the water tank 500. When the moisture absorption member 400 is partially immersed in the water 10 inside the water tank 500, the water 100 can be moved upwards by capillary action to be absorbed by the moisture absorption member 400.

The pump 600 may be disposed at one side of the water tank 500 to supply the water 10 from the water tank 500 to the moisture absorption member 400.

The pump 600 may be a decompression pump 600 and supplies the water 10 from the water tank 500 to the moisture absorption member 400 when driven by application of electric power thereto.

The water sterilization module 100 is disposed between the pump 600 and the moisture absorption member 400. The water sterilization module 100 serves to sterilize water prior to supply of the water to the moisture absorption member 400, and may include the water sterilization module 100 set forth above.

Pipes adapted to deliver water therethrough are disposed between the water tank 500 and the pump 600, between the pump 600 and the water sterilization module 100, and between the water sterilization module 100 and the moisture absorption member 400, respectively. When the pipes disposed between the water tank 500 and the pump 600, between the pump 600 and the water sterilization module 100, and between the water sterilization module 100 and the moisture absorption member 400 are referred as first to third pumps 710 to 730, respectively, the first pipe 710 is disposed at one end thereof in the water tank 500 and is connected at the other end thereof to the pump 600. The second pipe 720 is connected at one end thereof to the pump 600 and is connected at the other end thereto to the water inlet 125 of the water sterilization module 100. The third pipe 730 is connected at one end thereof to the water outlet 135 of the water sterilization module 100 and has the other end disposed adjacent to the moisture absorption member 400. Here, the other end of the third pipe 730 is provided in the form of a nozzle that can spray water into the moisture absorption member 400 therethrough.

In the air cooler 1000 having this structure, upon operation of the blower fan 300, external air is drawn into the housing 200 through the air inlet 210 by suction force of the blower fan 300. The air drawn into the housing 200 is delivered to the moisture absorption member 400. As the air is supplied to the moisture absorption member 400, water on an outer surface of the moisture absorption member 400 is vaporized by the air while absorbing latent heat from the surrounding area. Accordingly, the air around the moisture absorption member 400 is cooled due to loss of latent heat, and then is discharged from the air cooler through the air outlet 220. As a result, a user can experience cool air.

As described above, when used in the air cooler, the water sterilization module according to the embodiments of the present disclosure can sterilize water in the air cooler, thereby preventing proliferation of germs, microorganisms, and bacteria in the moisture absorption member or in water in the moisture absorption member even when water is supplied to the moisture absorption member later. Accordingly, the water sterilization module according to the embodiments of the present disclosure can prevent proliferation of germs or bacteria or generation of a bad odor, which can occur when the air cooler is used for a predetermined period of time or more.

Although the water sterilization module according to the embodiments of the present disclosure has been described as used in the air cooler in the above embodiment, it will be understood that the present disclosure is not limited thereto and the water sterilization module may be used in any other devices using water, such as humidifiers, without departing from the concepts of the disclosure.

Although some embodiments have been described herein, it should be understood that these embodiments are provided for illustration only and are not to be construed in any way as limiting the present disclosure, and that various modifications, changes, alterations, and equivalent embodiments can be made by those skilled in the art without departing from the spirit and scope of the disclosure.

Therefore, the scope of the present disclosure is not limited to the detailed description herein and should be defined only by the accompanying claims and equivalents thereto.

What is claimed is:

1. A water sterilization module comprising:
   a container comprising a water inlet a water outlet and a cover and configured to receive water therein; and
   a light source part mounted at a portion of the container to illuminate an interior of the container with light,
   wherein the water inlet has a larger diameter than a diameter of the water outlet, and
   wherein the water inlet has an extension extending downwardly of the cover such that a lower end of the extension is placed below a lower surface of the light source part, and
   wherein the extension has a lower part that has an inclined surface.

2. The water sterilization module according to claim 1, wherein the water inlet has a diameter twice as large as the diameter of the water outlet.

3. The water sterilization module according to claim 1, wherein the container comprises a lower receptacle having an open top and the cover covering the lower receptacle, and the light source part is mounted on the cover.

4. The water sterilization module according to claim 3, wherein the cover has an opening in which the light source part is mounted, and the light source part is mounted in the opening with a waterproof member placed therebetween.

5. The water sterilization module according to claim 3, wherein the lower receptacle comprises a bottom facing the cover and a sidewall extending upwards from the bottom, and the water outlet is disposed on the bottom.

6. The water sterilization module according to claim 5, wherein the bottom is inclined downwards from the sidewall towards the water outlet.

7. The water sterilization module according to claim 5, wherein the water outlet is disposed at a center of the bottom.

8. The water sterilization module according to claim 5, wherein the water inlet is vertically and horizontally spaced apart from the water outlet.

9. The water sterilization module according to claim 5, wherein the water inlet is disposed on the sidewall.

10. The water sterilization module according to claim 5, wherein the water inlet is disposed on the cover.

11. The water sterilization module according to claim 1, wherein the lower end of the extension is placed outside an illumination angle of light emitted from the light source part.

12. The water sterilization module according to claim 11, wherein the inclined shape of the lower end of the extension corresponds to the illumination angle of the light emitted from the light source part.

13. The water sterilization module according to claim 1, wherein the light source part comprises:
a main body having a light outlet;
a light source unit mounted on the main body and emitting the sterilizing light towards the light outlet; and
a window mounted on the main body and disposed between the light source unit and an interior of the container.

14. The water sterilization module according to claim 13, wherein the main body comprises:
a head disposed inside the container; and
a threaded portion passing through the container.

15. The water sterilization module according to claim 14, wherein the light source part further comprises a holder coupled to the threaded portion outside the container.

16. The water sterilization module according to claim 13, further comprising:
a waterproof member disposed between the window and the main body.

17. An air cooler comprising:
a housing having an air inlet and an air outlet;
a blower fan disposed in the housing to be adjacent to the air inlet;
a moisture absorption member disposed between the blower fan and the air outlet;
a water tank disposed in the housing to receive water therein;
a pump supplying water from the water tank to the moisture absorption member; and
a water sterilization module disposed between the water tank and the moisture absorption member to sterilize the water,
wherein the water sterilization module comprises:
a container comprising a water inlet a water outlet and a cover and configured to receive water from the water tank; and
a light source part mounted at a portion of the container to illuminate an interior of the container with light, and
wherein the water inlet has an extension extending downwardly of the cover such that a lower end of the extension is placed below a lower surface of the light source part,
wherein the extension has a lower part that has an inclined surface, and
wherein the container configured to adjust a water discharge time via the water outlet to be shorter than a water supply time via the water inlet.

18. The air cooler according to claim 17, further comprising:
a first pipe disposed between the water tank and the water sterilization module;
a second pipe disposed between the water sterilization module and the moisture absorption member;
the first pipe connected to the water inlet of the water sterilization module, and the second pipe connected to the water outlet of the water sterilization module.

19. The air cooler according to claim 17, wherein the water inlet has a diameter twice as large as a diameter of the water outlet.

* * * * *